United States Patent [19]

Vogel et al.

[11] Patent Number: 5,132,101
[45] Date of Patent: Jul. 21, 1992

[54] ACETYLENE-CUMULENE PORPHYCENE COMPOUNDS FOR PHOTODYNAMIC THERAPY

[75] Inventors: Emanuel Vogel, Cologne, Fed. Rep. of Germany; Alexander D. Cross, Atherton, Calif.; Norbert Jux, Bergisch Gladbach, Fed. Rep. of Germany; Eduardo Rodriguez-Val, Cologne, Fed. Rep. of Germany; Stefan Boehm, Cologne, Fed. Rep. of Germany; Wolfgang Hennig, Cologne, Fed. Rep. of Germany

[73] Assignee: Cytopharm, Inc., Menlo Park, Calif.

[21] Appl. No.: 578,346

[22] Filed: Sep. 6, 1990

Related U.S. Application Data

[63] Continuation-in-part of Ser. No. 541,037, May 4, 1990, abandoned.

[51] Int. Cl.$^5$ .................... C07D 209/56; A61K 31/40
[52] U.S. Cl. .......................................... 424/9; 604/20; 514/410; 540/472
[58] Field of Search ................ 540/472; 514/410; 424/9; 604/20

[56] References Cited

U.S. PATENT DOCUMENTS

| | | | |
|---|---|---|---|
| 3,592,930 | 7/1971 | Katz et al. | 514/171 |
| 3,989,815 | 11/1976 | Rajadhyaksha | 514/975 |
| 3,989,816 | 11/1976 | Rajadhyaksha | 514/975 |
| 3,991,203 | 3/1976 | Rajadhyaksha | 514/975 |
| 4,017,615 | 4/1977 | Shastri et al. | 514/171 |
| 4,411,893 | 10/1983 | Johnson et al. | 514/171 |
| 4,448,765 | 5/1984 | Ash et al. | 424/1.1 |
| 4,721,612 | 1/1988 | Janoff et al. | 424/450 |
| 4,798,891 | 1/1989 | Franck et al. | 540/472 |
| 4,837,028 | 6/1989 | Allen | 424/450 |
| 4,913,907 | 4/1990 | Jori et al. | 540/472 |
| 4,996,312 | 2/1991 | Sakata et al. | 540/145 |

FOREIGN PATENT DOCUMENTS 9006748 6/1990 PCT Int'l Appl. .................... 71/92

OTHER PUBLICATIONS

*Tetrahedron Letters No.* 50, (1975), pp. 4467–4470, "A Convenient Synthesis of Acetylenes: Catalytic Substitutions of Acetylenic . . . " Sonogashira et al.
*J. Org. Chem*, (1976), vol. 41, pp. 2826–2835, "Pyrrole Chemistry, the Cyanovinyl Aldehyde Protecting Groups", Paine et al.
*J. Org. Chem*, (1988), vol. 53, pp. 2787–2795, "5-Unsubstituted 2-Pyrrolecarboxaldehydes for Porphyrin Synthesis and the cyanovinyl . . . " Paine et al.
*Angew. Chem. Int. Ed. Engl.*, (1988), vol. 27, pp. 1170–1172, "Biomimentic Synethesis of an Octabinylogous Porphyrin with an Aromatic . . . " Knubel et al.
*Agnew. Chem*, (1988), vol. 100, pp. 1203, 1204 & 1211, "Biomimetische Synthese Eines Octabinylogen Porphyrins Mit Aromatischem . . . " Knubel et al.
*Angew. Chem. Int. Ed. Engl.*, (1986), 25, pp. 1100–1101, "Syntheis of a Fourfold Enlarged Porphyrin with an Extremely Large, Diamagnetic Ring . . . " Gosmann et al.
*Angew. Chem*, (1986), vol. 98, pp. 1107–1108, "Synthese Eines Virerfach Aufgeweiteten Porphyrins Mit Extrem Hohem Diamagnetischem . . . " Gosmann et al.
*J. Org. Chem.*, (1987), 52, pp. 710–711, "Synthesis of A [1,5,1,5]Platyrin, A 26-Electron Tetrapyrrolic Annulene", Schlessinger et al.
*J. Am. Chem. Soc.*, (1988), 110, pp. 5586–5588, "An 'Expanded Porphyrin': The Synthesis and Structure of a New Aromatic Pentadentate . . . ", Sessler et al.
*Tetrahedron Letters No. 44*, (1978), pp. 4225–4228, "The Synthesis of a 22-Electron Tetrapyrrolic Macrocycle, [1.3.1.3]Platyrin", Berger et al.
*Chemistry Letters*, (1973), pp. 1041–1044, "Reductive Coupling of Carbonyl Compounds to Pinacols and Olefins by Using . . ." Mukaiyama et al.

(List continued on next page.)

*Primary Examiner*—Robert T. Bond
*Assistant Examiner*—E. C. Ward
*Attorney, Agent, or Firm*—Oblon, Spivak, McClelland, Maier & Neustadt

[57] ABSTRACT

Dihydro- and tetrahydro-acetylene-cumulene porphycene compounds having the structure shown below

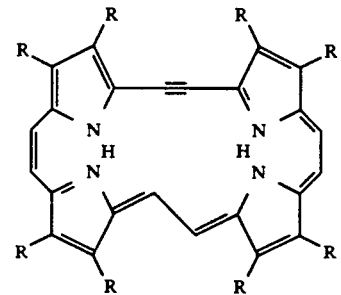

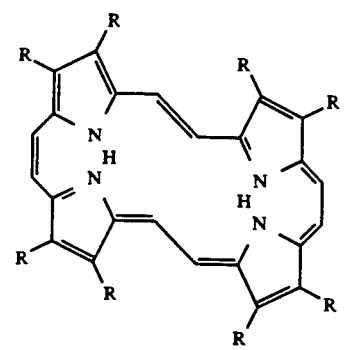

are useful as photogynamic therapy agents.

13 Claims, No Drawings

OTHER PUBLICATIONS

*J. Am. Chem. Soc.*, (1974), 96, pp. 4708-4709, "A New Method for the Reductive Coupling of Carbonyls to Olefins, Synthesis of -Carotene", McMurry et al.

*Organic Synthesis*, pp. 880-883, "Palladium Catalyst for Partial Reduction of Acetylenes", Lindlar et al.

*Cancer Research*, (1978), 38, pp. 2628-2633, "Phtoradiation Therapy for the Treatment of Malignant Tumors", Dougherty et al.

Review of Modical Pharmacology, 6th Ed. (Los Altos, Calif. lang Medical Publications, 1990) pp. 282-283 and 544-545.

Jux et al. Angow. Chem. 1990 29(12) pp. 1385-1381.

Vogel et al. Angew Chem. 1990 29(12) pp. 1387-1390.

Merck Index (Merck and Co., Inc. Rahway, N.J., 1989 p. 172.

Cooper, Spectroscopic Techniques for Organic Chemists (New York; J. Wiley and Sons, 1980) pp. 240-243.

Hawley, Condensed Chemical Dictionary (New York Van Nostrand Reinhold), 1980, p. 90.

Sessler JACS 1988, 110 5586-5588.

Achollai et al. JACS, 1985 107 6902-6908.

Berger et al. Tetrahadron Letters 44 4225-4228, 1978.

ACETYLENE-CUMULENE PORPHYCENE COMPOUNDS FOR PHOTODYNAMIC THERAPY

RELATED APPLICATIONS

This application is a continuation-in-part of U.S. patent application Ser. No. 07/541,037 filed May 4, 1990, now abandoned which is incorporated herein by reference in its entirety.

BACKGROUND OF THE INVENTION

1. Field of the Invention

The invention relates to novel porphycene compounds and pharmaceutical compositions containing these compounds which are useful for therapeutic treatment.

2. Discussion of the Background

During the past few years there has developed a widespread recognition that modern, though sophisticated, cancer diagnosis and treatments have served neither to reduce overall the number of cases of reported cancers in the U.S.A. nor, save the notable cases, the death rate. This is a disheartening result for the billions of dollars invested in conquering the disease. Moreover, surgery, radiotherapy and chemotherapy are all associated with major debilitating side effects such as trauma, severe immunosuppression or toxicity which are not easily surmounted by patients already compromised by ill-health.

Early work in the 1970's followed by rapidly expanding studies in the 1980's, has shown that photodynamic therapy (PDT) offers a viable, less toxic and generally less painful avenue to treatment of cancer. Not all cancers are candidates for PDT. However, intractable tumor masses (solid tumors, frequently characterized by poorly developed vascular system), sometimes inoperable, and with no good track record for treatment by established therapeutic procedures, appear to be for targets for PDT.

Dougherty et al (Cancer Res., 1978, 38, 2628) pioneered the field with infusion of photoactivatable dyes, followed by appropriate long wavelength radiation of the tumors (600+ nm) to generate a lethal shortlived species of oxygen which destroyed the neoplastic cells. Early experiments utilized a mixture termed haematoporphyrin derivative (HPD). The deficiencies of HPD, especially prolonged phototoxicity caused by retained HPD components in human skin led to its displacement by a purified fraction termed dihaematoporphyrin ether (DHE) which, although yielding improvements over HPD, nevertheless still suffered certain practical limitations. Relatively weak absorption in the wavelength range 600-700 nm, retention in dermal cells (potentially leading to phototoxicity) and uncertain chemical constitution are all known negative features. The great majority of the earlier PDT agents studied have been derived from natural sources (porphyrins, chlorins, purpurins, etc.) or from known chemicals originating in the dyestuffs industry (e.g., cyanine dyes).

As the deficiencies of these earlier agents has become apparent, it also becomes possible to define activity parameters for improved chemically pure photoactivatable dyes for PDT therapy, available by chemical synthesis. Moreover, the products of synthesis lend themselves more readily to further chemical structural manipulation than do the naturally-occurring starting materials which can be expensive and bear chemically sensitive constituents. The synthesis of novel porphycene macrocycles embracing four pyrrole rings, has been described by Vogel and coworkers. Alkylated porphycenes have also been prepared (R=H, Me, Et, n-Pr, n-octyl, phenyl) and the photochemical properties determined.

Pyrrole-containing ring systems larger than porphycene have also been prepared and evaluated as photosensitizers. Sessler et al have prepared and studied texaphyrin (J. Am. Chem. Soc., 1988, 110, 5586) and Woodward et al and Johnson et al have prepared and investigated the sapphyrin ring system. Additionally, the platyrin system has been studied by LeGoff (Tetrahedron, Lett., 1978, 4225; J. Org. Chem., 1987, 710) and vinylogous porphyrins have been studied by Franck (Angew. Chem., 1986, 98, 1107; Angew. Chem. Int. Ed. Eng., 1986, 25, 1100; Angew. Chem., 1988, 100, 1203; Angew. Chem. Int. Ed. Eng., 1988, 27, 1170).

A need continues to exist, therefore, for new compounds for use in PDT therapy, which compounds are easily available, have low intrinsic toxicity, are efficient photosensitizers for singlet oxygen production, have selective uptake in rapidly proliferating cells, are rapidly or at least moderately rapidly degraded and eliminated from the tissues after administration and which are available as chemically pure and stable compounds easily subject to synthetic modification.

SUMMARY OF THE INVENTION

Accordingly, one object of the present invention is to provide new and effective compounds for use in photodynamic therapy whose properties and characteristics approach the ideal characteristics of PDT dyes listed above.

This and other objects which will become apparent from the following specification have now been achieved with the dihydro and tetrahydro acetylene-cumulene porphycene (dihydro-ACP and tetrahydro-ACP) compounds of the present invention. The present compounds have utility as PDT dyes for use in cancer therapy and dermatological diseases, blood purification (elimination of viruses and bacteria, e.g., CMV, HIV, etc.) and for breakdown and removal of atherosclerotic plaques.

DETAILED DESCRIPTION OF THE PREFERRED EMBODIMENTS

While a substantial amount of research has been directed toward naturally occurring porphyrin-type compounds for use in PDT, it has now been discovered that certain derivatives of acetylene-cumulene porphycene have improved properties as PDT agents. The present porphycene compounds are aromatic and exhibit improved absorption and singlet oxygen photosensitization characteristics. The ACP compounds of the present invention exhibit improved absorption characteristics relative to known porphycene compounds, thereby making them suitable as photoactivatable dyes in PDT for both systemic and topical application. The compounds of the present invention exhibit a maximum wavelength absorption at between about 700 and 900 nm, preferably between about 750-800 nm. These longer wavelength absorption characteristics allows one to use the compounds of the present invention as PDT agents while minimizing the competing light absorption by blood and other tissues which absorb in the shorter wavelength regions below 600 nm. The compounds of the present invention are therefore superior to known porphycenes and porphyrins with regard to PDT therapy.

The compounds of the present invention have structures

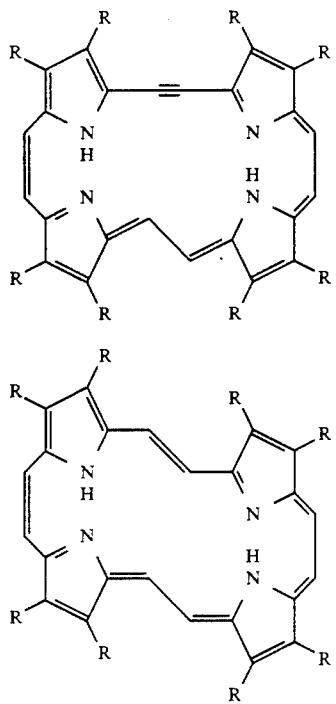

(2)

(3)

In the structures shown above, R is $C_{6-20}$ aryl, straight-chain or branched $C_{1-20}$ alkyl, or alkoxyalkyl of the formula $R'—O—(CH_2)_x—$, where $R'$ is $C_{1-10}$ alkyl and x is 1-6. Preferred compounds are those in which R is a $C_{1-10}$ alkyl and most preferred are compounds in which R is a $C_{1-6}$ alkyl group.

The compounds of the present invention can be prepared by reductively coupling appropriate acetylenic dipyrroledialdehydes having the structure below where R is as defined above and then reducing the acetylene cumulene compound formed.

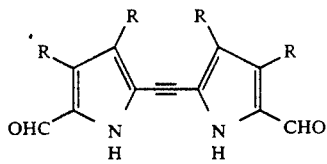

Reductive coupling using two dipyrroledialdehydes is accomplished using low-valent titanium compounds which result in the formation of the tetrapyrrole macrocyclic ring structure of the present compounds. The coupling reaction of two acetylenic dipyrroledialdehydes can be accomplished using a McMurry coupling reaction (J. E. McMurry, M. P. Fleming, J. Am. Chem. Soc., 96, (1974) 4707; T. Mukaiyama, T. Sato, J. Hanna, Chem. Lett., 1973, 1041). Typically, reductive coupling can be carried out using a titanium amalgam prepared by reacting titanium tetrachloride with an additional metal such as zinc, copper, aluminum and salts thereof. The reductive coupling reaction is carried out in a non-reactive solvent such as a hydrocarbon or ether solvent. Typical solvents include alkanes having from 5-10 carbon atoms such as pentane, hexane, heptane, etc. as well as ether solvents such as diethyl ether, crown ethers, diglyme and THF. If desired, the coupling reaction can be heated to facilitate the reaction, i.e. the reaction can be conducted under reflux conditions.

The appropriate acetylenic dipyrroledialdehydes can be prepared according to known synthetic chemistry from pyrrolaldehydes having the appropriate R group in the 3- and 4-positions. Scheme 1 illustrates the synthesis of the acetylene-cumulene compounds of the present invention from pyrrolaldehydes (see J. B. Paine, III, R. B. Woodward, D. Dolphin, J. Org. Chem., 41 (1976) 2826). The pyrrolaldehyde is iodinated (J. B. Paine, III, D. Dolphin, J. Org. Chem., 53 (1988) 2787) and the iodoaldehyde produced is then reacted with acetylene in the presence of a catalyst to form the desired acetylenic dipyrroledialdehyde (K. Sonogashira, N. Hagihara, Tetrahedron Lett., 1975, 4467).

As indicated in Scheme 1, reductive coupling of the acetylenic dipyrroledialdehydes is thought to initially form a true tetrapyrrole macrocycle shown in brackets which then spontaneously air oxidizes to form the acetylene-cumulene porphycene of the present invention. The compound of the present invention can then be isolated in substantially pure form by conventional purification techniques such as chromatography, recrystallization, etc.

Scheme 1

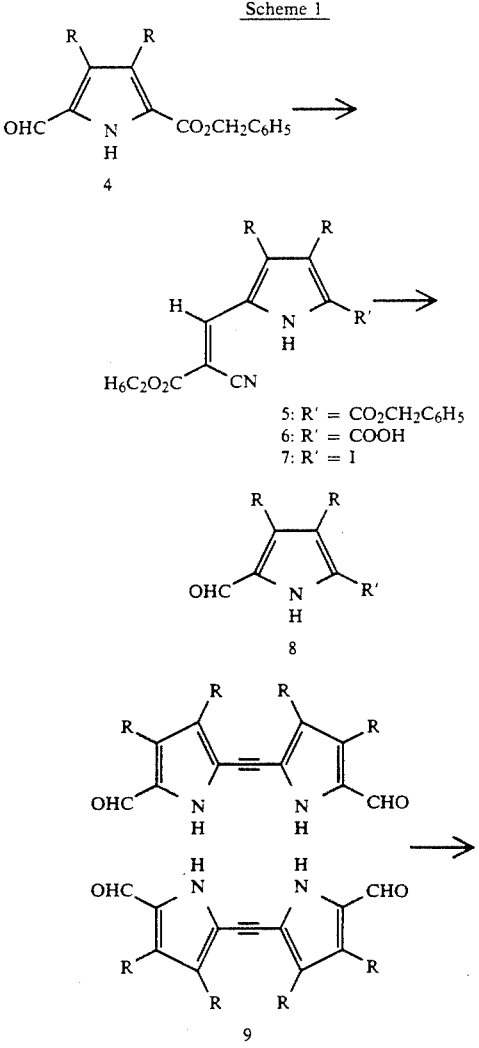

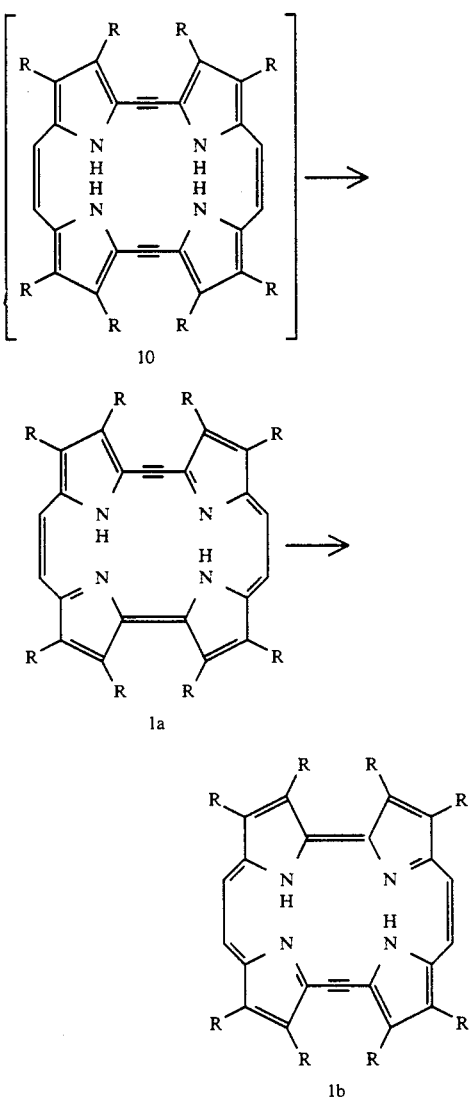

-continued
Scheme 1

10

1a

1b

The dihydro-ACP and tetrahydro-ACP compounds of the present invention are prepared by reducing the ACP compounds prepared as shown in Scheme 1. Any reducing agent and any reaction conditions may be used which enable reduction of the cumulene and/or the acetylene groups to the corresponding conjugated dihydro-ACP and tetrahydro-ACP compounds. Reducing agents which are capable of reducing a cumulene or acetylene group to the alkene are well known to those skilled in the art. For example, Compound 1 shown in Scheme 1 can conveniently be reduced by dissolving Compound 1 in a polar solvent and hydrogenating in the presence of a poisoned heterogeneous catalyst under a hydrogen atmosphere to reduce the cumulene group and thereby give a dihydro-ACP compound. A typical poisoned catalyst is Lindlar's-catalyst (Lindlar, H. and Dubuis, R., Org. Synth., V (1973) 880).

The tetrahydro-ACP compounds of the present invention can be prepared by further reducing the dihydro-ACP compounds. Preferably, the tetrahydro-ACP compounds are prepared by using the same catalyst as used to prepare the dihydro-ACP compounds. For example, dihydro-ACP compounds can be prepared by first reducing the ACP compounds prepared according to Scheme 1 using a poisoned catalyst. The dihydro-ACP compound can then be further reduced under a hydrogen atmosphere in the presence of additional catalyst to produce the tetrahydro-ACP compound. Alternatively, the tetrahydro-ACP can be prepared by directly reducing the ACP compound.

Isolation of both the dihydro-ACP and tetrahydro-ACP compounds of the present invention can be effected by conventional chromatography and recrystallization processes.

The reduced acetylene-cumulene porphycene compounds of the present invention are capable of generating singlet oxygen under appropriate irradiation conditions, each, therefore, constituting a photoactivatable dye for use in PDT.

The ability of the dihydro-ACP and tetrahydro-ACP compounds of the present invention to generate singlet oxygen is surprising in view of the fact that ACP compound 1 does not generate singlet oxygen. In spite of the similarity between the structures of Compound 1 and the dihydro-ACP and tetrahydroACP compounds of the present invention, only the dihydro- and tetrahydro-ACP compounds are effective in generating singlet oxygen and therefore useful as PDT agents.

THERAPEUTIC FORMULATIONS

Therapeutic compositions containing the compounds of the present invention include liposome or microvesicle preparations, dispersions, solutions for parenteral injection, etc. and including topical dermatological preparations.

Parenteral Solutions

The photoactivable porphycene dyes generally are used with additional solvents and adjuvants to prepare solutions suitable for intravenous injection. A number of solvents and co-solvents that are miscible with water and suitable surfactants can be used to achieve solutions for parenteral use. The most important solvents in this group are ethanol, polyethylene glycols of the liquid series and propylene glycol. A more comprehensive listing includes acetone, dimethyl acetamide, dimethyl formamide, dimethyl sulfoxide ethanol, glycerin, polyethylene glycol 300, and 400, propylene glycol, sorbitol, polyoxyethylene sorbitan fatty acid esters such as laurate, palmitate, stearate, and oleate, polyoxyethylated vegetable oil, sorbitan monopalmitate, 2-pyrrolidone; n-methyl-2-pyrrolidine; n-ethyl-1-pyrrolidine and tetrahydrofurfuryl alcohol.

Other additives may be necessary to enhance or maintain chemical stability and physiological suitability. Examples are antioxidants, chelating agents, inert gases, buffers and isotonicifiers.

Examples of antioxidants and typical concentration ranges include acetone sodium bisulfite (0.1–0.8%), ascorbic acid (0.05–1.0%), monothioglycerol (0.1–1.0%), potassium metabisulfite (0.05–0.1%), propyl gallate (0.02%), sodium bisulfite (0.01–1.0%), sodium formaldehyde sulfoxylate (0.03–0.1%), sodium metabisulfite (0.02–0.25%), sodium sulfite (0.01–0.1%), sodium thioglycolate (0.05–0.1%).

Examples of chelating/complexing agents and typical concentration ranges include edetate sodium (0.005–0.1%), edetate calcium disodium (0.005%–0.01%), gentisic acid ethanolamide (1.0%–2.0%), niacinamide (1.0%–2.5%), sodium citrate (0.01%–2.5%), citric acid (0.001%–1.0%).

Examples of inert gases are nitrogen and carbon dioxide.

Buffers are used primarily to stabilize a solution against the chemical degradation that might occur if the pH changed appreciably. Buffer systems employed normally have as low a buffer capacity as feasible in order to not disturb significantly the body buffer systems when injected. The buffer range and effect of the buffer on activity must be evaluated. Appropriate adjustment is useful to provide the optimum conditions for pH dependent partition into the target malignant tissues or lesion area.

Examples of such buffer systems include the following acids: acetic, adipic, ascorbic, benzoic, citric, glycine, lactic, tartaric, hydrochloric, phosphoric, sulfuric, carbonic and bicarbonic; and their corresponding salts such as: potassium, sodium, magnesium, calcium and diethanolamine salts.

Osmoticity is of great importance and hypotonic solutions usually have their tonicity adjusted by the addition of salts such as sodium chloride, potassium chloride, magnesium chloride and calcium chloride and sugars such as dextrose, lactose, mannitol and sorbitol.

When the solution will be dispensed from multiple dose containers, antimicrobial agents in bacteriostatic or fungistatic concentrations must be added. Among the compounds and concentrations most frequently employed are phenylmercuric acid (0.002–0 01%), thimerosal (0.01%), benzethonium chloride (0.01%), benzalkonium chloride (0.01%), phenol or cresol (0.5%), chlorbutanol (0.5%), benzyl alcohol (2.0%), methyl p-hydroxybenzoate (0.18%), and propyl p-hydroxybenzoate (0.02%).

After the solution of the porphycene with its solvents and additives has been compounded, the solution is filtered to remove particulate matter above 2 μm in size and a further step eliminating particulate matter down to 0.2 μm can eliminate microorganisms and accomplish cold sterilization. The solution is filled under aseptic conditions. The final solution can be additionally sterilized in its final container by thermal methods such as autoclaving or non-thermal methods such as ionizing radiation. The process of freeze drying (lyophilization) can be employed to avoid adverse thermal and oxidative decomposition and provide enhanced stability and improved solubility.

The following formula provides an example of the utilization of various solvents and additives such as have been heretofore mentioned in the creation of a suitable parenteral solution of the porphycene. The formula is by way of example only and is not limiting to this invention. Suitable combinations and variations are obvious to those skilled in the art.

| Formula example for octaethyltetrahydro acetylene cumulene porphycene (octaethyltetrahydro-ACP) | |
|---|---|
| | Grams |
| Octaethyltetrahydro ACP | 0.1 |
| Tetrahydrofurfurylalcohol | 40.0 |
| Polysorbate 20 | 1.0 |
| Sodium chloride | 0.9 |
| Citric acid buffer | 0.1 |
| water* enough to make 100 ml | |

*water may be water for injection, bacteriostatic water for injection or sterile water for injection.

Method of Preparation

1. Dissolve porphycene in tetrahydrofurfuryl alcohol and polysorbate 20, using heat and stirring as needed.
2. Dissolve sodium chloride and citrate buffer in water.*
3. Add the water solution slowly with stirring and heat as necessary to the solution.
4. Sterile fill using aseptic conditions and use terminal sterilization as needed.

This solution is suitable for a broad dosage range such as 0.1–10 mg/kg and preferably 0.2–5.0 mg/kg and may be infused as such or added to suitable large volume parenteral solutions such as dextrose, saline, ringers solutions for slower intravenous administration. Suitable solutions are described, for example, in REMINGTON'S PHARMACEUTICAL SCIENCES, 15th Ed., Easton: Mack Publishing Co. incorporated herein by reference.

Topical Formulations

The porphycene compounds of the present invention may be formulated for topical application in penetrating solvents or in the form of a lotion, cream, ointment or gel containing a sufficient amount of the porphycene compound to be effective for PDT therapy.

Suitable penetrating solvents are solvents for the porphycene compound which will enhance percutaneous penetration of the porphycene compound. Solvents which have this property include dimethyl sulfoxide, dimethyl acetamide, dimethyformamide and 1-methyl-2-pyrrolidone and to a lesser extent propylene glycol. Additional solvents include substituted azacycloalkan-2-ones having from 5 to 7 carbons in the cycloalkyl group such as 1-dodecylazacycloheptan-2-one (AZONE) and other azacycloalkan-2-ones such as described in U.S. Pat. No. 3,989,816 incorporated herein by reference and having the structure shown below

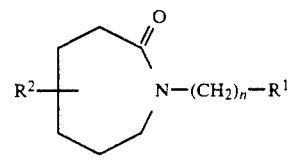

wherein $R^1$ is a straight or branch chain alkyl group having from 1 to 18 carbons or aryl group having from 6 to 10 carbons;

$R^2$ is H or lower alkyl having from 1 to 4 carbons; and n is an integer from 0 to 10.

Also included are N-bis-zaocyclopentan-2-onyl alkanes described in U.S. Pat. No. 3,989,815 (hereby incorporated by reference) and having the formula:

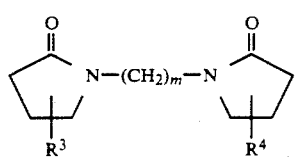

wherein $R^3$ and $R^4$ are each H or a lower alkyl group having from 1 to 4 carbons; and m is a positive integer of from 1 to 18. Also included are 1-substituted azacyclopentan-2-ones described in U.S. Pat. No. 3,991,203 (hereby incorporated by reference) and represented by formula:

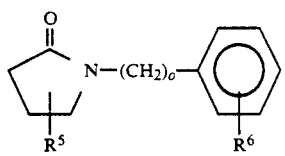

wherein
$R^5$ and $R^6$ are each H or lower alkyl having from 1 to 4 carbons; and
o is a positive integer from 0 to 10.

Also included are water-soluble tertiary amine oxides described in U.S. Pat. No. 4,411,893 (hereby incorporated by reference) and represented by the following formulas:

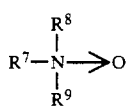

wherein
$R^7$, $R^8$ and $R^9$ are each saturated or unsaturated aliphatic groups optionally containing ether or amide linkages and pendent hydroxyl groups, and the total number of carbon atoms of $R^7$, $R^8$ and $R^9$ does not exceed 28, and

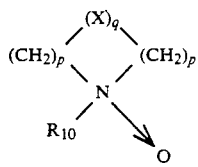

wherein X is —O— or —N($R^{11}$)—;
$R^{10}$ and $R^{11}$ are each saturated or unsaturated aliphatic groups having from 1 to 18 carbons and optionally containing ether or amide linkages and pendent hydroxyl groups; and
p is 0 or 1;
q is 2, 3, or 4; and
r is 2 or 3.

The topical formulations contain a sufficient amount of the porphycene compound to be effective in PDT therapy. Generally, concentrations in the range of 0.001 to 5 wt. %, preferably from about 1 to 5 wt. % may be used. Typical lotion and cream formulations are show below.

| Parts by Weight | LOTION Ingredient |
|---|---|
| 5 | polyoxylene-40-stearate |
| 3 | sorbitan monostearate |
| 12 | *mixture of lanolin, mineral oil and lanolin alcohol |
| 6 | cetyl alcohol |
| 20 | soybean oil |
| 53.7 | water |
| 0.2 | methyl paraben |
| 0.1 | propyl paraben |

*AMERCOL BL (Amerchol Corp. Edison, N.J.)

| Parts by Weight | CREAM Ingredient |
|---|---|
| 3 | polyoxylene-40-stearate |
| 2.5 | sorbitan monostearate |
| 10 | soybean oil |
| 10 | *mixture of lanolin, mineral oil and lanolin alcohol |
| 1 | cetyl alcohol |
| 73.2 | water |
| 0.2 | methyl paraben |
| 0.1 | propyl paraben |

*AMERCOL BL (Amerchol Corp. Edison, N.J.)

Additional topical formulations which may be used in conjunction with the porphycene compounds of the present invention are disclosed in U.S. Pat. Nos. 3,592,930 and 4,017,615 (hereby incorporated by reference).

Liposome or Microvesicle Preparations

Liposomes and methods of preparing liposomes are known and are discribed for example in U.S. Pat. No. 4,452,747 and U.S. Pat. No. 4,448,765 incorporated herein by reference. Liposomes are microvesicles which encapsulate a liquid within lipid or polymeric membranes. The porphycene compounds of the present invention may be incorporated into lipsome microvesicles and used in this form for both topical and parenteral application. Topical and parenteral liposome preparations are known in the art.

U.S. Pat. No. 4,837,028 discloses injectable liposome formulations having enhanced circulation time. The liposomes have a size of about 0.08-0.5 microns, contain at least 50 mole % of a membrane rigidifying component such as sphingomyelin and further contain about 5-15 mole % ganglioside $G_{M1}$. Liposome preparations for encapsulating sparingly soluble pharmaceutical compounds are disclosed in U.S. Pat. No. 4,721,612. The specifiction of these U.S. patents is incorporated herein by reference.

After administration of a therapeutically effective amount of one or more of the porphycene compounds in the pharmaceutical composition or preparation, to a patient having a treatable condition such as a solid tumor (cancer) or psoriasis, for example, the patients affected body area is exposed to a therapeutically sufficient amount of light having an appropriate wavelength for absorption by the particular porphycene compound used. Suitable wavelengths are generally from about 650 to about 900 nm, preferably from about 700 to about 900 nm. Irradiation of the accumulated porphycene generates singlet oxygen which is thought to be the actual lethal species responsible for destruction of the neoplastic cells.

Photodynamic therapy using the porphycene compounds of the present invention has a number of advantages. The porphycene compound itself is minimally toxic in the unexcited state. Each porphycene molecule can be repeatedly photoactivated and lead each time to cell-lethal events, that is, the generation of singlet molecular oxygen. The half-life of singlet molecular oxygen is approximately four microseconds in water at room temperature. The target cell is therefore affected without the opportunity for migration of the lethal singlet molecular oxygen to neighboring healthy tissue cells. Preferably, the singlet oxygen molecules rupture chemical bonds in the target cell wall, mitochondria or DNA resulting in destruction of the target cell. Destruction of target cell tissue commences promptly upon irradiation of the porphycene compounds and ceases abruptly when irradiation is stopped. Photodynamic therapy using the compounds of the present invention is therefore selective and minimally toxic to healthy tissue. Singlet oxygen molecules produced which do not react rapidly decay to harmless ground state oxygen molecules.

A variety of phototherapy and irradiation methodologies are known to those skilled in the art and can be used with the novel porphycene compounds of the present invention. The time and duration of therapy and repetition of the irradiation treatment can be selected by the therapist (physician or radiologist) according to known photodynamic therapy criteria. The dosage of the porphycene compound may be varied according to the size and location of the target tissues which are to be destroyed and the method of administration. Generally, the dosage will be in the range of 0.05–10 mg of porphycene compound per kilogram of body weight, more preferably in the range of 0.1–5.0 mg/kg.

Irradiation generally takes place not less than one hour nor more than four days after parenteral administration of the porphycene compound. Usually, phototherapy is begun approximately 3 hours to 48 hours after administration of the photodynamic therapy agent. With topically administered dye, radiation may commence as soon as 10 minutes after dye application for treatment of psoriasis, genital warts, bacterial infections, etc. Exposure to non-therapeutic light sources should be avoided immediately following phototherapy to minimize light toxicity. Appropriate draping of the patient can be used to limit the area affected by phototherapy.

Light sources which are appropriate for use are well known in the art and may vary from white light sources with appropriate filters to lasers. As noted above, preferred wavelengths are from 600 to 950 nm, preferably from about 600 to about 800 nm. The total amount of light which is applied to the affected area will vary with the method used and the location of the tumor or topical lesion. Generally, the amount of light is in the range of about 50 to 1000 J-cm$^2$, preferably in the range of 100 to 350 J-cm$^2$.

Having generally described this invention, a further understanding can be obtained by reference to certain specific examples which are provided herein for purposes of illustration only and are not intended to be limiting unless otherwise specified. Procedures which are constructively reduced to practice herein are described in the present tense and procedures which have been carried out in the laboratory are set forth in the past tense.

EXAMPLES

Example 1

Octaethyl ACP

2-Benzyloxycarbonyl-3,4-diethyl-5-formyl-pyrrole was reacted with NCCH$_2$CO$_2$Et in ethanol in the presence of methylamine to provide compound 5 shown in Scheme 1 in the form of yellow needles. When recrystallized from ethanol (81% yield) compound 5 was found to have a melting point of 108° C.

Compound 5: $^1$H-NMR (300 MHz, CDCl$_3$): δ = 10.26 (br s, 1H), 8.00 (s, 1H), 7.43, 7.36, 7.31 (m, 5H), 5.35 (s, 2H), 4.33 (q, 2H), 2.73 (q, 2H), 2.59 (q, 2H), 1.36 (t, 3H), 1.13 (t, 3H), 1.12 (t, 3H); MS (70 eV); m/z 380 (M$^+$, <1%), 91 (100); IR (KBr): γ=3426, 2207, 1714, 1595 cm$^{-1}$; UV/VIS (CH$_2$Cl$_2$):λ$_{max}$=240 nm (ε=15100), 382 (32900).

Compound 5 was then hydrogenated over Pd/C under a hydrogen pressure of 1 atmosphere for 4 hours at 25° C. to provide compound 6 in 98% yield.

Compound 6: $^1$H-NMR (300 MHz, CDCl$_3$): δ = 11.39 (br s, 1H), 10.24 (br s, 1H), 8.03 (s, 1H), 4.34 (q, 2H), 2.76 (q, 2H), 2.62 (q, 2H), 1.37 (t, 3H), 1.16 (t, 3H), 1.15 (t, 3H); MS (70 eV): m/z 290 (M$^+$, 64%), 200 (100); IR (KBr): γ=3419, 2615, 2210, 1724, 1666 cm$^{-1}$; UV/VIS (CH$_2$Cl$_2$) λ$_{max}$=238 nm (ε=14700), 380 32000).

Compound 6 was then iodinated using ICl in acetic acid/sodium acetate for 20 minutes at 70°C. to give compound 7 in 85% yield. 2-Iodo-3,4-diethyl-5-formyl-pyrrole was then prepared by stirring compound 8 with sodium hydroxide in methanol/water under reflux for 3 hours to provide compound 8 in 70% yield.

Compound 7 (Isomers E/Z 58:42): $^1$H-NMR (300 MHz, CDCl$_3$) δ = 12 49 (Z, br s, 1H), 9.62 (E, br s, 1H), 7.81 (E, s, 1H), 7.12 (Z, s, 1H), 4.32 (Z, q, 2H), 4.30 (E, q, 2H), 2.61 (E, q, 2H), 2.60 (Z, q, 2H), 2.40 (E and Z, q, J =2H each), 1.36 (Z, t, 3H), 1.33 (E, t, 3H), 1.13 (E, t, 3H), 1.12 (Z, t, 3H), 1.07 (E and Z, t, 3H each); MS (70 eV); m/z 372 (M$^+$, 8%), 157 (100); IR (KBr): γ=3737, 2205, 1707, 1685 cm$^2$; UV/VIS (CH$_2$Cl$_2$): λ$_{max}$=227 nm (ε=10200), 260 (1000), 306 (3300), 402 (41200).

Compound 8: $^1$H-NMR (300 MHz, CDCl$_3$): δ=9.54 (br s, 1H), 9.38 (s, 1H), 2.73 (q, 2H), 2.38 (q, 2H), 1.21 (t, 3H), 1.07 (t, 3H); MS (70 eV); m/z 277 (M$^+$, 100%), 262 (84); IR (KBr): γ=3246, 1620, 1367 cm$^{-1}$ UV/VIS (CH$_2$Cl$_2$): λ$_{max}$=226 nm (ε=4100), 313 (19700).

Bis(3,4-diethyl-5-formyl-2-pyrryl) acetylene was then prepared by passing acetylene into a solution of compound 8 in diethylamine in the presence of bis(triphenylphosphine)palladium dichloride and copper iodide at 45° C. The reaction was carried out for 7 hours. The non-polymeric amine product was the desired acetylenic dipyrroledialdehyde which was isolated as yellow-orange needles following chromatographic separation on silica gel with ethyl acetate:pentane (1:1), and recrystallization from ethyl acetate. The melting point was 255° C. with decomposition. The yield was 22%.

Compound 9: $^1$H-NMR (300 MHz, [D$_6$]-DMSO): δ=12.30 (br s, 1H), 9.60 (s, 1H), 2.70 (q, 2H), 2.52 (q, 2H), 1.13 (t, 3H), 1.12 (t, 3H); MS (70 eV); m/z 324 (M$^+$, 100%); IR (KBr): γ=3233, 1614, 1442, 1277 cm$^{-1}$ UV/VIS (CH$_2$Cl$_2$): λ$_{max}$=400 nm (ε=37200), 381 (36000), 283 (20700), 257 (18700), 246 (17700).

The coupling reagent was prepared by suspending 65 mg (10 mmol) activated zinc and 65 mg (0.7 mmol) anhydrous copper (I) chloride in 40 ml absolute tetrahydrofuran (THF). Titanium tetrachloride (0.54 ml, 5 mmol) was then added slowly and the mixture heated under reflux for 3 hours. Compound 9 (162 mg, 0.5 mmol) was then added in small portions. After 10 minutes, the product was hydrolyzed with 40 ml ammonia/water and the mixture was extracted with chloroform. Chromatographic purification on silica gel with dichloromethane:hexane (1:1) followed by recrystallization from benzene yielded 35 mg octaethyl-ACP in the form of blue crystals. Purification was carried out by chomatography on silica gel with carbon disulfide to give a purified product recrystallizing from benzene in the form of blue needles with a metallic luster. The melting point was >300° C. with decomposition.

Compound 1: $^1$H-NMR (300 MHz, CS$_2$/CD$_2$Cl$_2$) δ=9.99 (s, 4H, H-11), 4.50 (q, 8H, H-3a), 4.16 (q, 8H, H-2a), 2.34 (t, 12H, H-3b), 2.28 (s, 2H, NH), 2.03 (t, 12H, H-2b); $^{13}$C-NMR (75.5 MHz), CS$_2$/CD$_2$Cl$_2$) δ=143.28, 142.76, 140.82, 126.72, 111.85, 105.75, 22.02, 21.02, 19.43, 18.41; MS (70 eV); m/z 582 (M$^+$, 100%), 291 (6); IR (CsI): γ- 2962, 2067, 1479, 1267, 1216, 1200, 1116, 994, 941, 932 cm$^{-1}$; UV/VIS (CH$_2$Cl$_2$): λ$_{max}$=766 nm (ε=79400), 724 (73300), 677 (38900), 651 (15300)sh, 619 (4900)sh, 492 (6200)sh, 439 (76500), 405 (188700), 381 (45600)sh, 297 (12800).

EXAMPLE 1A

Alternative synthesis of cis,trans,cis,trans-2,3,8,9,14,15,20,21-octaethyl[22]porphyrin-(2.2.2.2) by reductive tetramerisation of 3,4-diethyl-2,5-diformylpyrrole

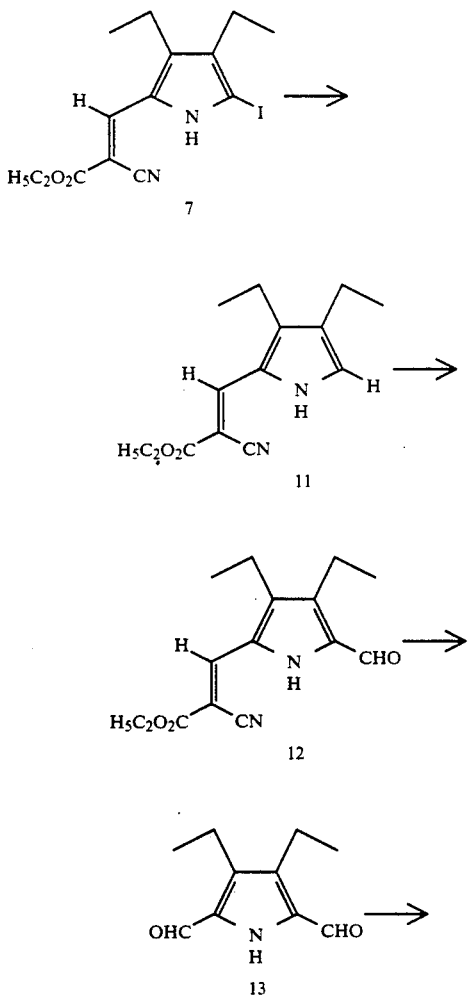

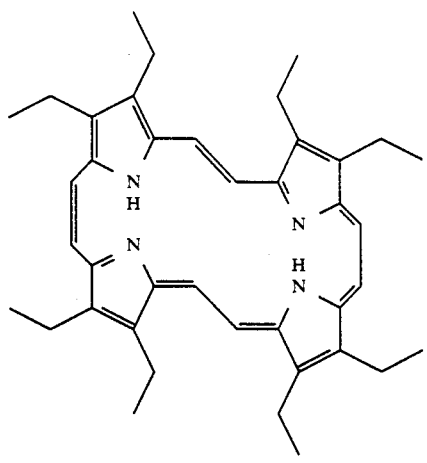

3

2-(2-Cyan-2-ethoxycarbonyl)-3,4-diethyl-pyrrole (11)

55.7 g (0.15 mol) of compound 7 were mixed with 49.1 g (0.76 mol) zinc dust and treated with 325 ml of glacial acetic acid over a period of 20 minutes. The zinc was filtered off and washed with methanol. After pouring two liters of water in the filtrate, the precipitate was filtered off. Recrystallization from ethanol yielded 35 g (95%) of compound 11 in the form of yellow needles with a melting point of 118° C.

Compound 11: $^1$H-NMR (300 MHz, CDCl$_3$) δ=9.73 (br s, 1H), 7.96 (s, 1H), 6.99 (d, 1H), 4.29 (q, 2H), 2.59 (q, 2H), 2.43 (q, 2H), 1.33 (t, 3H), 1.17 (t, 3H), 1.10 (t, 3H); MS (70 eV); m/z 246 (M$^+$, 83%); IR (KBr): γ=3387, 2206, 1714, 1584, 1237 cm$^{-1}$; UV/VIS (CH$_2$Cl$_2$); λ$_{max}$=227 nm (ε=3400), 385 (35000).

2-(2-Cyan-2-ethoxycarbonyl)-3,4-diethyl-5-formylpyrrole (12)

15 ml (160 mmol) phosphorous oxychloride were added dropwise for a period of 20 minutes to 13 ml (160 mmol) dimethylformamide at a temperature of 0° C. The mixture was stirred for another 15 minutes at room temperature and then 100 ml of dichloroethane were added. A solution of 10 g (40 mmol) of compound 11 in 50 ml dichloroethane were added dropwise. After gentle reflux for 15 minutes, the mixture was poured into 500 ml of a 4-molar sodium acetate solution and heated for a further 15 minutes. The organic layer was separated, washed with water and yielded after evaporation of the solvent, a brown oil, which was directly used for the next step without purification.

3,4-Diethyl-2,5-diformylpyrrole

Compound 12 was stirred and refluxed under argon atmosphere with a mixture of sodium hydroxide/methanol for 2 hours. The organic layer was separated, neutralized and washed with water. Chromatographic purification and recrystallization from ethanol yielded 3.6 g (50%) of compound 13 in the form of a light-brown crystalline powder with a melting point of 105°-106° C.

Compound 13: $^1$H-NMR (300 MHz, CDCl$_3$); δ=10.02 (br s, 1H), 9.86 (s, 2H), 2.74 (q, 4H), 1.21 (t, 6H); MS (70 eV); m/z 179 (M$^+$, 100%); IR (KBr);

γ=3261, 1675, 1649, 1470, 1220 cm⁻¹; UV/VIS (CH₂Cl₂); λ=241 nm (ε=19300), 320 (1400).

cis,trans,cis,trans-2,3,8,9,14,15,20,21-Octaethyl-22]porphyrin-(2.2.2.2) (3)

The coupling reagent was prepared by suspending 9.1 g (140 mmol) activated zinc and 0.7 g (7 mmol) copper(I) chloride in 400 ml absolute tetrahydrofuran (THF). Titanium tetrachloride (7.6 ml, 70 mmol) was then added slowly and the mixture heated under reflux for 3 hours. Compound 13 (900 mg, 5 mmol) was dissolved in 40 ml THF and added in drops for 30 minutes. The product was hydrolysed with 100 ml ammonia/water and the mixture extracted with dichloromethane. Chromatographic filtration on silica gel with dichloromethane followed by recrystallization from dichloromethane/hexane yielded 7 mg (1%) of compound 3 in the form of a microcrystalline blue powder with a metallic luster.

EXAMPLE 2

In a manner analogous to Example 1, 2-benzyloxycarbonyl-3,4-dimethyl-5-formyl-pyrrole, 2-benzyloxycarbonyl-3,4-dipropyl-5-formyl-pyrrole, 2-benzyloxycarbonyl-3,4-dibutyl-5-formy-pyrrole, 2-benzyloxycarbonyl-3,4-dipentyl-5-formyl-pyrrole, 2-benzyloxycarbonyl-3,4-dihexyl-5-formyl-pyrrole, 2-benzyloxycarbonyl-3,4-di(2-ethylhexyl)-5-formyl-pyrrole and 2-benzyloxycarbonyl-3,4-didecyl-5-formyl-pyrrole are reduced, iodinated and reacted with acetylene to form bis(3,4-dimethyl-5-formyl-2-pyrryl)acetylene, bis(3,4-dipropyl-5-formyl-2-pyrryl)acetylene, bis(3,4-dibutyl-5-formyl-2-pyrryl)acetylene, bis(3,4-dipentyl-5-formyl-2-pyrryl)acetylene, bis(3,4-dihexyl-5-formyl-2-pyrryl)acetylene, bis(3,4-di(2-ethylhexyl)-5-formyl-2-pyrryl)acetylene and bis(3,4-didecyl-5-formyl-2-pyrryl)acetylene.

These acetylene dipyrroledialdehydes are then coupled in a manner analogous to Example 1 to form octamethyl-ACP, octapropyl-ACP, octabutyl-ACP, octapentyl-ACP, octahexyl-ACP, octa(2-ethylhexyl)-ACP, and octadecyl-ACP.

EXAMPLE 3 cis,trans,cis-5-Dehydro-2,3,8,9,14,15,20,21-octaethyl[22]porphyrin(2.2.2.2)(Octaethyldihydro-ACP)

(1)

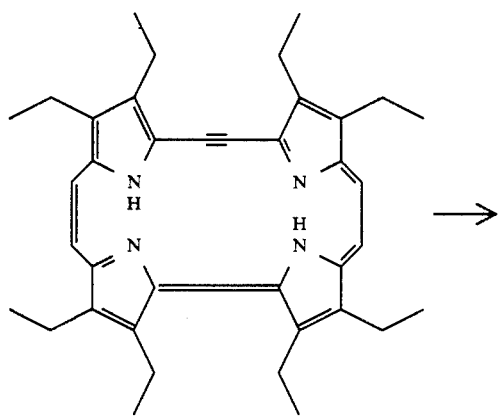

→

-continued (2)

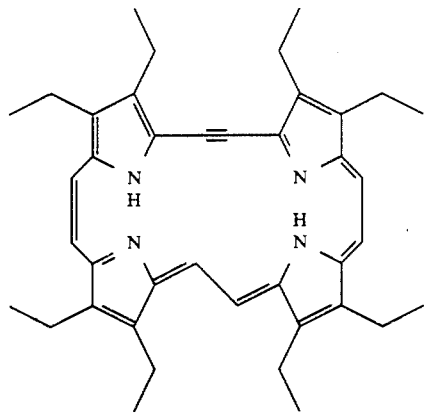

58 mg (0.1 mmol) of 5,17-Didehydro-2,3,8,9,14,15,20,21-octaethyl[22]porphyrin-(2.2.2.2) were dissolved in 80 ml of tetrahydrofuran. The solution was stirred with 100 mg of Lindlar-catalyst under hydrogen (1 atm, room temperature) for two hours. The catalyst was filtered off and washed with dichloromethane until the rinsings were colorless. The solvent was removed and cis,trans,cis-5-dehydro-2,3,8,9,14,15,20,21-octaethyl-[22]porphyrin-(2.2.2.2porphyrin-(2.2.2.2) was isolated by column chromatography (4×15 cm, silica, carbon disulfide). After recrystallization from benzene the yield of Compound 2 is 15 mg (25%); mp. 292° C. (decomp.) Compound 2: ¹H-NMR (300 MHz. CS₂/CD₂Cl₂) δ=11.63 (d, 1H, H-17), 9.93, 9.81, 9.71, 9.63 (4d, 4H, H-11,12,23,24), 4.64 (s br, ¹H, NH), 4.63, 4.46, 4.31, 4.27, 4.12, 4.11, 4.07, 4.06 (8q, 16H, CH₂), 2.35, 2.34, 2.27, 2.15, 1.99, 1.97 (6t, 18H, CH₃), 2.00 (t, 6H, CH₃), 0.67 (s br, 1H, NH'), −7.15 (d, 1H, H-18); ¹³C-NMR (75.5 MHz, CS₂/CD₂Cl₂); δ=146.60, 146.10, 144.44, 144.00, 143.22, 142.56, 141.86 (2C), 141.60, 141.22, 140.61, 139.98, 139.62, 138.90, 129.59, 122.73, 115.89, 114.52, 114.33, 113.76, 109.08, 106.78, 104.63, 101.41, 23.04, 21.82, 21.78, 20.98, 20.94, 20.77, 20.66, 20.32, 19.40, 19.32, 19.12 (2C), 19.06, 18.20, 18.13, 16.92; MS (70 eV); m/z 584 (M+, 100%), 292 (4); IR (KBr) γ=2960, 2929, 2867, 2100, 1479, 1370, 1270, 1199, 1052, 991, 940 cm⁻¹; UV/VIS (CH₂Cl₂): λ_max=372 nm (ε=2000) sh, 424 (135600), 448 (80900) sh, 673 (30800), 721 (44200), 768 (48300).

EXAMPLE 4

Cis,trans,cis,trans-2,3,8,9,14,15,20,21-octaethyl[22]porphyrin-(2.2.2.2)(Octaethyltetrahydro-ACP)

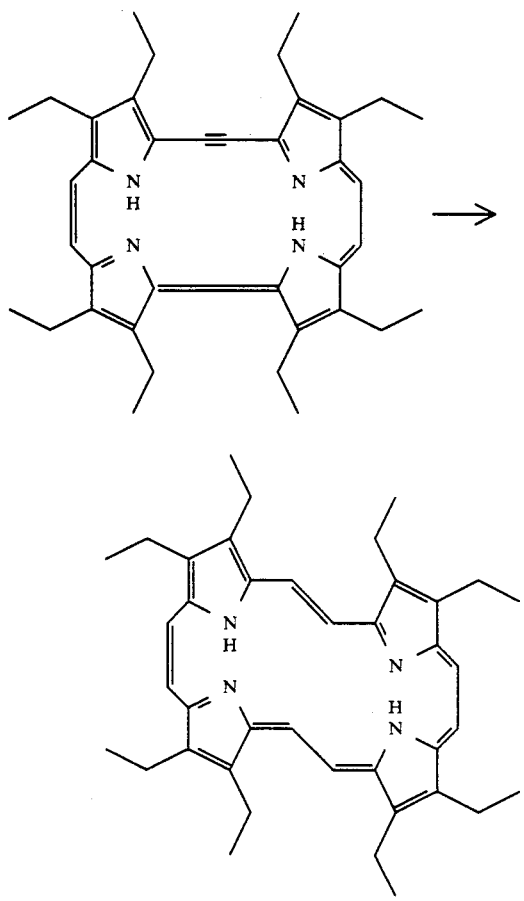

58 mg (0.1 mmol) of 5,17-Didehydro-2,3,8,9,14,15,20,21-octaethyl[22]porphyrin-(2.2.2.2) were dissolved in 80 ml of tetrahydrofuran. The solution was stirred with 100 mg of Lindlar-catalyst under hydrogen (1 atm, room temperature) for two hours. After the addition of further 100 mg of Lindlar-catalyst the reaction was continued for three hours. The catalyst was filtered off and washed with dichloromethane until the rinsings were colorless. The solvent was removed and cis, trans, cis, trans-2,3,8,9,14,15,20,21-octaethyl[22]porphyrin-(2.2.2.2) was isolated by column chromatography (4×8 cm, silica, carbon disulfide). After recrystallization from benzene the yield of Compound 3 was 21 mg (35%); mp. 287° C. (decomp.).

Compound 3 has a singlet oxygen quantum yield of 0.2 ($\phi_\Delta$).

Compound 3: $^1$H-NMR (300 MHz, CS/CD$_2$Cl$_2$) $\delta$=11.70 (d, 2H, H-5), 9.88, 9.83 (2d, 4H, H-11,12), 4.69, 4.28 (2q, 8H, H-3a, 8a), 4.14 (q, 8H, H-2a, 9a), 2.36, 2.14 (2t, 12H, H-3b,8b), 2.01, 1.99 (2t, 12H, H-2b,9b), 1.43 (s br, 2H, NH), −7.50 (d, 2H, H-6); $^{13}$C-NMR (75.5 MHz, CS$_2$/CD$_2$Cl$_2$) $\delta$=147.26, 145.61, 144.99, 140.48, 140.24, 139.93, 139.85, 139.48, 116.09, 113.84, 113.30, 108.96, 23.10, 20.90, 20.66, 20.46, 19.37, 19.30 (2C), 16.81; MS (70 eV): m/z 586 (M+, 100%), 293 (18); IR (KBr): $\gamma$=2963, 2932, 2871, 1471. 1283, 1195, 1054, 1006,.985, 937, 806, 619 cm−; UV/VIS (CH$_2$Cl$_2$): $\lambda_{max}$=270 nm ($\epsilon$=14400), 417 (79800) sh, 440 (207900), 464 (104400), 482 (41600) sh, 579 (2200) sh, 618 (4100) sh, 656 (19500) sh, 672 (38900), 685 (26500) sh, 719 (16600) sh, 726 (17100), 790 (57200).

EXAMPLE 5

In a manner analogous to Examples 3 and 4, octamethyldihydro-ACP, octapropyldihydro-ACP, octabutyldihydro-ACP, octapentyldihydro-ACP, octahexyldihydro-ACP, octa(2-ethylhexyl)dihydro-ACP and octadecyldihydro-ACP are prepared by reducing the corresponding octamethyl-ACP, octapropyl-ACP, octabutyl-ACP, octapentyl-ACP, octahexyl-ACP, octa(2-ethylexyl)-ACP and octadecyl-ACP prepared in Example 2.

EXAMPLE 6

Each of the octaalkyldihydro-ACP compounds prepared in Example 5 are further hydrogenated in the presence of additional Lindlar-catalyst under a hydrogen atmosphere to prepare the octamethyltetrahydro-ACP, octapropyltetrahydro-ACP, octabutyltetrahydro-ACP, octapentyltetrahydro-ACP, octahexyltetrahydro-ACP, octa(2-ethylhexyl)tetrahydro-ACP and octadecyltetrahydro-ACP compounds.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An acetylene-cumulene porphycene compound having the structure shown below:

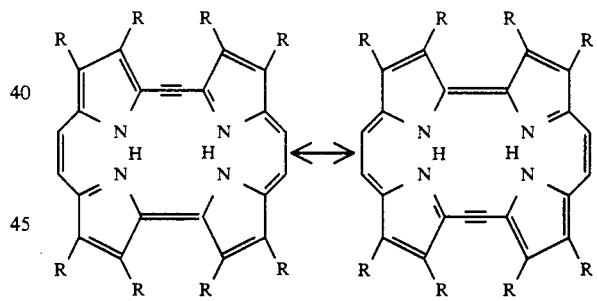

wherein R is C$_{6-20}$ aryl, straight-chain or branched C$_{1-20}$ alkyl or alkoxyalkyl of the formula R′—O—(CH$_2$)$_x$—, where R′ is C$_{1-6}$ alkyl and x is 1–6.

2. The compound of claim 1, wherein R is C$_{1-10}$ alkyl.
3. The compound of claim 1, wherein R is C$_{1-6}$ alkyl.
4. A compound having the structure shown below:

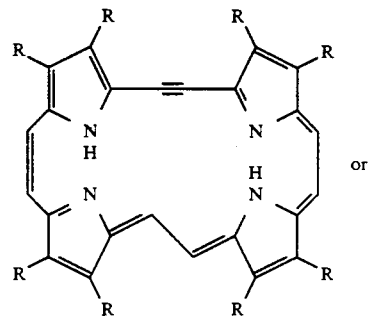

or

-continued

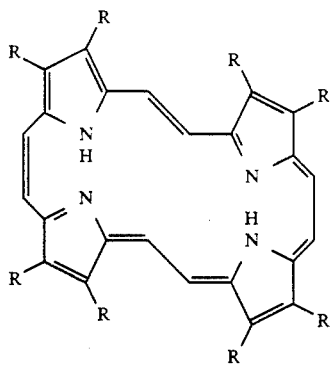

wherein R is a $C_{6-20}$ aryl, straight-chain or branched $C_{1-20}$ alkyl or alkoxyalkyl of the formula $R'—O—(CH_2)_x—$, where $R'$ is $C_{1-6}$ alkyl and x is 1-6.

5. The compound of claim 4, wherein R is $C_{1-10}$ alkyl.
6. The compound of claim 5, wherein R is $C_{1-6}$ alkyl.
7. A pharmaceutical composition comprising an effective amount of a compound having the structure shown below:

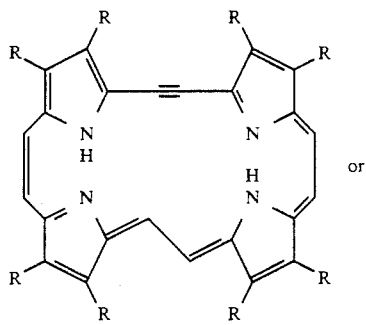 or

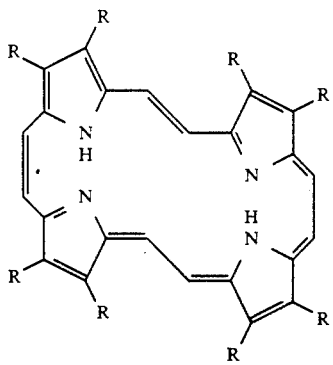

wherein R is $C_{6-20}$ aryl, straight-chain or branched $C_{1-20}$ alkyl or alkoxyalkyl of the formula $R'—O—(CH_2)_x—$ where $R'$ is $C_{1-6}$ alkyl, x is 1-6, and a pharmaceutically acceptable carrier.

8. The composition of claim 7, wherein R is $C_{1-10}$ alkyl.
9. The composition of claim 8, wherein R is $C_{1-6}$ alkyl.
10. The composition of claim 7, wherein said carrier is a penetrating solvent which enhances percutaneous penetration of said compound.
11. A method of photodynamic therapy, comprising the steps of
administering to a mammal in need thereof, an effective amount of a having the formula shown below:

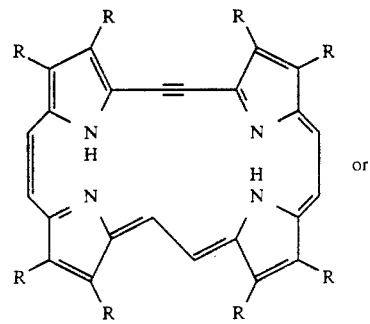 or

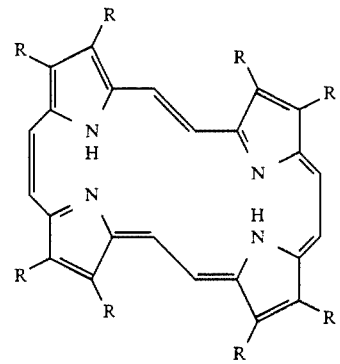

wherein R is $C_{6-20}$ aryl, straight-chain or branched $C_{1-20}$ alkyl, or alkoxyalkyl of the formula $R'—O—(CH_2)_x—$, where $R'$ is $C_{1-6}$ alkyl and x is 1-6, and
irradiating said animal with light at a wavelength in the absorption spectrum of said reduced acetylene-cumulene porphycene.

12. The method of claim 11, wherein said administering is topical administration.
13. The method of claim 11, wherein said administering is enteral, parenteral, intramuscular or oral administration.

* * * * *